(12) United States Patent
Geiger

(10) Patent No.: US 9,108,023 B1
(45) Date of Patent: Aug. 18, 2015

(54) GASTRIC NASAL TUBE SUPPORT SYSTEM

(76) Inventor: Robert B. Geiger, Richmond, KY (US)

( * ) Notice: Subject to any disclaimer, the term of this patent is extended or adjusted under 35 U.S.C. 154(b) by 569 days.

(21) Appl. No.: 13/477,427

(22) Filed: May 22, 2012

(51) Int. Cl.
*A61M 25/02* (2006.01)
*G02C 11/00* (2006.01)
*A61M 16/06* (2006.01)

(52) U.S. Cl.
CPC ........... *A61M 25/02* (2013.01); *A61M 16/0672* (2013.01); *G02C 11/00* (2013.01); *A61M 2025/024* (2013.01); *A61M 2025/0206* (2013.01); *A61M 2025/0226* (2013.01); *A61M 2210/0618* (2013.01); *Y10S 128/26* (2013.01)

(58) Field of Classification Search
CPC .............. A61M 16/0461; A61M 16/0666; A61M 16/0672; A61M 16/0683; A61M 2210/0618; A61M 25/02; A61M 2025/0206; A61M 2025/0213; A61M 2025/0226; A61M 2025/024; A61M 2025/0253; A61M 2025/026; A61M 2025/028; G02C 11/00; Y10S 128/26
USPC ......... 604/79, 94.01, 174, 179, 516; 351/158; 128/207.18
See application file for complete search history.

(56) References Cited

U.S. PATENT DOCUMENTS

| | | | |
|---|---|---|---|
| 2,168,705 A | | 8/1939 | Francisco et al. |
| 2,259,817 A | | 10/1941 | Hawkins |
| 3,209,755 A | * | 10/1965 | McCarthy et al. ............ 604/174 |
| 4,106,505 A | | 8/1978 | Salter et al. |
| 4,156,426 A | | 5/1979 | Gold |
| 4,282,871 A | | 8/1981 | Chodorow et al. |
| 4,537,192 A | | 8/1985 | Foster |
| 4,559,941 A | | 12/1985 | Timmons et al. |
| 4,708,446 A | * | 11/1987 | Timmons et al. ............ 351/158 |
| 5,437,273 A | | 8/1995 | Bates et al. |
| 5,438,979 A | * | 8/1995 | Johnson et al. .......... 128/207.18 |
| 6,067,985 A | | 5/2000 | Islava |
| 6,669,712 B1 | | 12/2003 | Cardoso |
| 6,684,883 B1 | | 2/2004 | Burns |
| 2010/0326434 A1 | | 12/2010 | Couts |

* cited by examiner

*Primary Examiner* — Kami A Bosworth
(74) *Attorney, Agent, or Firm* — Robert C. Montgomery; Montgomery Patent & Design, LP

(57) ABSTRACT

A gastric nasal tube support system designed to hold various medical tubes that enter through a user's nose without the use of adhesive tape includes a pair of eye goggles that are held around the rear of a user's head with an elastic strap. A front portion of the goggles includes a clip structure spanning both sides of the nose area. The clip structure can hold various medical tubes such as gastric nasal tubes, oxygen tubes, drainage tubes, feeding tubes, or the like so that they remain in place as they enter the nasal cavity. The clip structure facilitates quick removal and replacement of tubes.

18 Claims, 2 Drawing Sheets

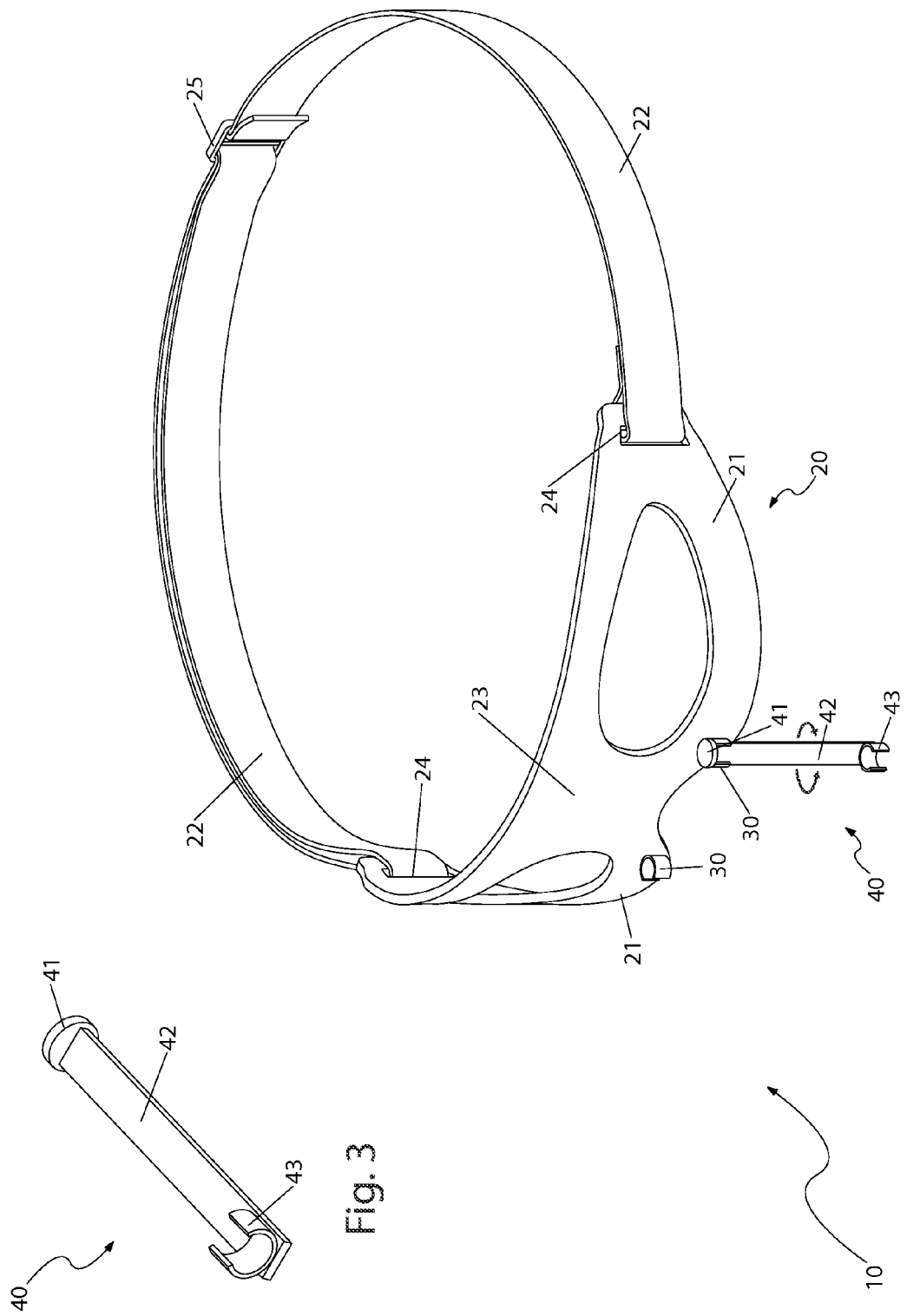

GASTRIC NASAL TUBE SUPPORT SYSTEM

RELATED APPLICATIONS

There are currently no applications co-pending with the present application.

FIELD OF THE INVENTION

The present invention relates generally to gastric nasal tube support systems, and in particular, to systems that support a gastric nasal tube without the use of adhesive tape.

BACKGROUND OF THE INVENTION

During a hospital visit or other long-term extended stay in a medical facility, patients must often endure having various tubes inserted into their nasal cavity. Such tubes include nasogastric tubes for use in feeding and administering drugs as well as oxygen tubes used to deliver concentrated oxygen. Such tubes are typically held in place to the patient's nose and face area using sections of adhesive tape. Each time the various tubes are removed and/or replaced, new pieces of tape are utilized. As one could imagine, such tape quickly becomes irritating leading to chaffing, redness, and other discomfort for the patient. Accordingly, there exists a need for a means by which patients who have various medical tubes inserted into their nasal cavity can be spared the discomfort of adhesive tape. The development of the gastric nasal tube support system fulfills this need.

There have been several attempts in the past to invent gastric nasal tube support systems that do not rely on the use of adhesive tape. U.S. Pat. No. 2,168,705, issued in the name of Francisco, describes a nasal inhaler. This patent features a support structure similar to a frame for eyeglasses that is supported by the ears along with a tube assembly that is supported by the frame above the patient's nose. This patent does not disclose eyewear that is supported to a patient's head with an adjustable elastic strap.

U.S. Pat. No. 2,259,817, issued in the name of Hawkins, describes an adjustable head attachment for oxygen tubes. This patent features a tube assembly that is inserted into a patient's nose and is supported by a non-elastic band at the patient's forehead. This patent does not disclose eyewear that is supported to a patient's head with an adjustable elastic strap.

U.S. Pat. No. 4,559,941, issued in the name of Timmons, describes an eyeglass frame and nasal cannula assembly. This patent features a pair of conventional appearing eyeglasses that mask a cannula tube assembly to allow a patient to inconspicuously use a portable oxygen tank. This patent does not disclose eyewear that is supported to a patient's head with an adjustable elastic strap.

U.S. Pat. No. 6,684,883, issued in the name of Burns, describes a nasal cannula headband apparatus. This patent features a tube assembly that is inserted into a patient's nose and is supported by a friction supported non-elastic band at the patient's forehead. This patent does not disclose eyewear that is supported to a patient's head with an adjustable elastic strap.

While these support systems fulfill their respective, particular objectives, each of these references suffer from one (1) or more disadvantages. Accordingly, there exists a need for gastric nasal tube support system without the disadvantages as described above. The development of the present invention substantially departs from the conventional solutions and in doing so fulfills this need.

SUMMARY OF THE INVENTION

The inventor has recognized the aforementioned inherent problems and lack in the art and observed that there is a need for a gastric nasal tube support system.

Accordingly, it is an object of the present embodiments of the invention to solve at least one (1) of these problems. To achieve the above objectives, it is an object of the present invention to provide a system that supports a gastric nasal tube without the use of adhesive tape.

Another object of the present invention is to provide an apparatus comprising eyewear that further comprises a plurality of tube holders.

Yet still another object of the present invention is to provide a plurality of frame clips that are able to accept the tube holders, are generally "C"-shaped, and are attached to an upper front surface of the eyewear.

Yet still another object of the present invention is where the tube holder comprises a shoulder, an extension, and a tube holder clip.

Yet still another object of the present invention is where the extension positions the tube holder clip below the nose of the patient.

Yet still another object of the present invention is where the tube holder clip is generally "C"-shaped to accommodate the exterior surface of the tube and position it into the patient's nose.

Yet still another object of the present invention is where the tube holders are designed to accommodate nasal gastric tubes along with other medical tubes including but not limited to oxygen tubes and feeding tubes.

Yet still another object of the present invention is to secure the apparatus to a patient's head using an adjustable strap.

Yet still another object of the present invention is where the adjustable strap is preferably made of an elastic material and comprises an adjustment buckle to alter the size of the strap.

Yet still another object of the present invention is to provide a method of utilizing the apparatus that may be achieved by performing the following steps: placing the strap around the patient's cranium and the frame over their eyes with the bridge upon the nose; adjusting the strap via the adjustment buckle as desired; positioning a tube holder into each or a single frame clip with the tube holder clip facing away from the patient; routing the tube into the nose at a desired length and portion of the length of tube into the tube holder clip; removing the tube and apparatus as desired; and, providing patients who utilize various medical tubes routed through the nasal cavity on a long-term basis increased comfort in a manner which is quick, easy, and effective.

Further objects and advantages of the present invention will become apparent from a consideration of the drawings and ensuing description.

BRIEF DESCRIPTION OF THE DRAWINGS

The advantages and features of the present invention will become better understood with reference to the following more detailed description and claims taken in conjunction with the accompanying drawings in which like elements are identified with like symbols and in which:

FIG. 2 is a perspective view of the medical tube support 10, according to a preferred embodiment of the present invention; and, FIG. 3 is a perspective view of a tube holder 40 removed from the medical tube support 10, according to a preferred embodiment of the present invention

DESCRIPTIVE KEY

Figure 1:
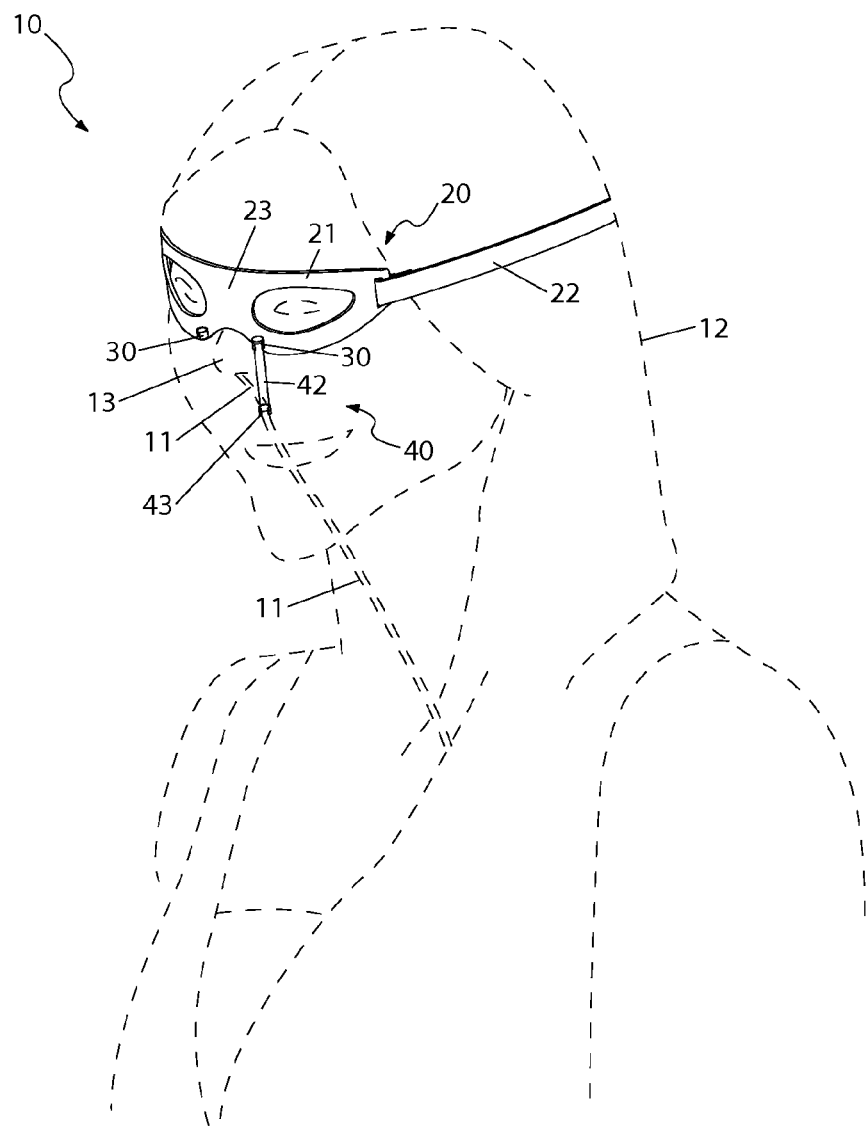
FIG. 1 is an environmental view of a medical tube support 10, according to a preferred embodiment of the present invention.

- 10 medical tube support
- 11 tube
- 12 patient
- 13 nose
- 20 eyewear
- 21 frame
- 22 strap
- 23 bridge
- 24 aperture
- 25 adjustment buckle
- 30 frame clip
- 40 tube holder
- 41 shoulder
- 42 extension
- 43 tube holder clip

DETAILED DESCRIPTION OF THE PREFERRED EMBODIMENT

The best mode for carrying out the invention is presented in terms of its preferred embodiment, herein depicted within FIGS. 1-3, and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention describes a medical tube support (herein described as the "apparatus") 10, which provides a means to hold medical tubing 11 without irritating a patient 12.

Referring now to FIG. 1, an environmental view of the apparatus 10, according to the preferred embodiment of the present invention, is disclosed. The apparatus 10 includes eyewear 20 and a pair of tube holders 40. The apparatus 10 is positioned upon the face of the patient 12 similar to the wearing of common sports goggles. It is known that the apparatus 10 may be fabricated in various sizes to accommodate various sized patients 12 and to accommodate various sized tubing 11. Medical tubing 11 such as nasal gastric tubes, oxygen tubes, feeding tubes, or similar tubes which are routed through the nose 13 may be utilized without limiting the scope of the apparatus 10. The apparatus 10 positions the tube 11 into the nose 13 in a position which eliminates skin irritation, adhesive residue, redness, and general discomfort associated with the use of adhesive tape.

Referring now to FIG. 2, a perspective view of the apparatus 10, according to the preferred embodiment of the present invention, is disclosed. The eyewear 20 include a frame 21 which surround each eye of the patient 12, a strap 22 which secures the eyewear 20 around the patients 12 cranium, and a bridge 23 which positions the eyewear 20 upon the nose 13 to assist in supporting the eyewear 20. The eyewear 20 is preferably fabricated from a soft plastic as to be comforting to the patient 12. The frame 21 is preferably lens-less. Each side portion of the frame 21 includes an aperture 24 which enables the strap 22 to be threaded through. The strap 22 is preferably an elastic band with an adjustment buckle 25 which encompasses the patients 12 cranium. An upper front surface of the frame 21 includes a pair of opposing and integrally molded "C"-shaped frame clips 30. Each frame clip 30 is able to accept a tube holder 40 which is utilized to position and secure the tubing 11.

As illustrated in FIG. 3, a pair of tube holders 40 accompanies the apparatus 10 to enable tubes 11 to be positioned within a desired nostril or within each nostril. Each tube holder includes a shoulder 41, an extension 42, and a tube holder clip 43. The tube holder 40 is preferably fabricated from a soft rubber, yet other materials may be utilized without limiting the scope of the apparatus 10. The shoulder 41 is disc-shaped and integrally molded to the extension 42 which is generally rectangular. The tube holder clip 43 is integrally molded to a lower side surface of the extension 42. The extension 42 positions the tube holder clip 43 slightly below the nose 13 of the patient 12. The extension 42 is slid through the frame clip 30 which allows the shoulder 41 to rest on an upper surface of the frame clip 30 further suspending the tube holder 40 upon the eyewear 20. The tube holder clip 43 is "C"-shaped which partially clutches an exterior surface of tube 11 to route the tube 11 into the nose 13 and retain the tube 11 into the desired position.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the apparatus 10, it would be installed as indicated in FIG. 1.

The method of installing and utilizing the apparatus 10 may be achieved by performing the following steps: acquiring the apparatus 10; placing the strap 22 around the patient's 12 cranium and the frame 21 over their eyes with the bridge 23 upon the nose 13; adjusting the strap 22 via the adjustment buckle 25 as desired; positioning a tube holder 40 into each or a single frame clip 30 with the tube holder clip 43 facing away from the patient 12; routing the tube 11 into the nose 13 at a desired length and portion of the length of tube 11 into the tube holder clip 43; removing the tube 11 and apparatus 10 as desired; and, providing patients 12 who utilize various medical tubes 11 routed through the nasal cavity on a long-term basis increased comfort in a manner which is quick, easy, and effective.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:
1. A support for medical tubing, comprising:
   eyewear, comprising:
      a frame, comprising a pair of eye portions each having an eye aperture and a bridge spanning between said eye portions;
      an adjustable strap attached to opposing sides of said frame; and, a pair of "C"-shaped frame clips located on an upper front surface of said frame; and,
a pair of tube holders removably attachable to said pair of frame clips;
wherein said eyewear is adapted to be worn on the face of a patient about an eye region;
wherein said strap is adapted to secure said eyewear to a head of said patient; and,
wherein said pair of tube holders is adapted to secure and assist in positioning medical tubing in place to prevent skin irritation from unintended movement.

2. The support of claim 1, wherein said frame further comprises a pair of strap apertures permitting the routing of said strap therethrough.

3. The support of claim 1, further comprising a lens within each of said pair of eye apertures.

4. The support of claim 1, wherein said pair of frame clips and said frame are a unitary construction.

5. The support of claim 4, wherein said frame further comprises a soft plastic construction.

6. The support of claim 1, wherein each of said pair of tube holders further comprises:
an elongated portion;
a shoulder centrally located at a first perimeter edge of said elongated portion, having a width greater than said frame clip; and,
a tube holder clip attached to a first side of said elongated portion adjacent to a second perimeter edge opposite said first perimeter edge;
wherein said shoulder prevents downward removal of said tube holder from said frame clip;
wherein said tube holder clip prevents upward removal of said tube holder from said frame clip;
wherein said tube holder clip is adapted to secure said medical tubing therein; and,
wherein said elongated portion comprises a length to position said tube holder clip subjacent to a nose of said patient when said eyewear is worn and said tube holder is attached to said eyewear.

7. The support of claim 6, wherein said shoulder is disc-shaped.

8. The support of claim 7, wherein said tube holder clip is "C"-shaped.

9. The support of claim 8, wherein said shoulder, said tube holder clip, and said elongated portion are a unitary construction.

10. The support of claim 9, wherein said pair of tube holders further comprises a soft plastic construction.

11. A support for medical tubing, comprising:
eyewear, further comprising:
a frame, comprising a pair of eye portions each having an eye aperture and a bridge spanning between said eye portions;
an adjustable strap attached to opposing sides of said frame; and,
a pair of frame clips located on an upper front surface of said frame; and,
a pair of tube holders removably attachable to said eyewear, each further comprising:
an elongated portion;
a shoulder centrally located at a first perimeter edge of said elongated portion, having a width greater than a frame clip; and,
a tube holder clip attached to a first side of said elongated portion adjacent to a second perimeter edge opposite said first perimeter edge;
wherein said shoulder prevents downward removal of said tube holder from said frame clip;
wherein said tube holder clip prevents upward removal of said tube holder from said frame clip;
wherein said elongated portion comprises a length to position said tube holder clip subjacent to a nose of said patient when said eyewear is worn and said tube holder is attached to said eyewear;
wherein said eyewear is adapted to be worn on the face of a patient about an eye region;
wherein said strap is adapted to secure said eyewear to a head of said patient;
wherein said pair of frame clips supports and secures said medical tubing; and,
wherein said tube holder clip of each of said pair of tube holders is adapted to secure and assist in positioning medical tubing in place to prevent skin irritation from unintended movement.

12. The support of claim 11, wherein said frame further comprises a pair of strap apertures permitting the routing of said strap therethrough.

13. The support of claim 11, further comprising a lens within each of said pair of eye apertures.

14. The support of claim 11, wherein said pair of frame clips and said frame are a unitary construction.

15. The support of claim 14, wherein said frame further comprises a soft plastic construction.

16. The support of claim 11, wherein said shoulder, said tube holder clip, and said elongated portion are a unitary construction.

17. The support of claim 16, wherein said pair of tube holders further comprises a soft plastic construction.

18. A method of securing and positioning medical tubing to prevent skin irritation during unwanted movement of said medical tubing comprises the following steps:
providing eyewear, comprising:
a frame, comprising a pair of eye portions each having an eye aperture and a bridge spanning between said eye portions;
an adjustable strap attached to strap apertures located at opposing sides of said frame; and,
a pair of "C"-shaped frame clips located on an upper front surface of said frame;
providing a pair of tube holders each removably attachable to one of said pair of frame clips, each further comprising:
an elongated portion;
a disc-shaped shoulder centrally located at a first perimeter edge of said elongated portion, having a width greater than said frame clip; and,
a "C"-shaped tube holder clip attached to a first side of said elongated portion adjacent to a second perimeter edge opposite said first perimeter edge;
wearing said eyewear;
installing at least one of said pair of tube holders into one of said pair of frame clips, such that said shoulder rests upon a top surface of said frame clip and said tube holder clip is subjacent to a nose; and,
inserting medical tubing into said tube holder clip.

* * * * *